United States Patent
Hall

[19]

[11] Patent Number: 5,811,259

[45] Date of Patent: Sep. 22, 1998

[54] BIOCHEMICAL REACTOR

[75] Inventor: Peter Jans Hall, Danville, Calif.

[73] Assignee: EcoMat, Inc., Hayward, Calif.

[21] Appl. No.: 902,092

[22] Filed: Jul. 29, 1997

[51] Int. Cl.$^6$ .............................. C12M 3/00; B01F 3/00
[52] U.S. Cl. .................... 435/41; 435/289.1; 435/295.1; 435/295.3; 435/299.1; 435/80.1; 422/227; 422/229; 422/238; 422/239; 210/903
[58] Field of Search ............................... 435/801, 289.1, 435/295.1, 299.1, 813, 295.3, 297.1, 41; 422/225, 227, 229, 238, 239; 210/903

[56] References Cited

U.S. PATENT DOCUMENTS

| | | | |
|---|---|---|---|
| 3,841,999 | 10/1974 | Bennett et al. | 210/17 |
| 4,008,159 | 2/1977 | Besik | 210/7 |
| 4,009,099 | 2/1977 | Jeris | 210/3 |
| 4,039,438 | 8/1977 | Anderson | 210/11 |
| 4,173,531 | 11/1979 | Matsch et al. | 210/5 |
| 4,181,604 | 1/1980 | Onishi et al. | 210/8 |
| 4,188,289 | 2/1980 | Besik | 210/7 |
| 4,207,180 | 6/1980 | Chang | 435/295.1 |
| 4,253,966 | 3/1981 | Lebesgue et al. | 210/610 |
| 4,415,454 | 11/1983 | Fuchs | 210/616 |
| 4,454,038 | 6/1984 | Shimodaira et al. | 210/150 |
| 4,469,599 | 9/1984 | Gros et al. | 210/610 |
| 4,482,458 | 11/1984 | Rovel et al. | 210/603 |
| 4,576,717 | 3/1986 | Collin et al. | 210/610 |
| 4,707,252 | 11/1987 | Durot et al. | 210/151 |
| 4,715,958 | 12/1987 | Fuchs | 210/605 |
| 4,756,831 | 7/1988 | Menzel et al. | 210/617 |
| 4,814,278 | 3/1989 | Hamamoto et al. | 435/295.1 |
| 4,954,257 | 9/1990 | Vogelpohl et al. | 210/607 |
| 4,970,000 | 11/1990 | Eppler et al. | 210/605 |
| 5,232,586 | 8/1993 | Malone | 210/151 |
| 5,248,613 | 9/1993 | Roubicek | 435/295.1 |
| 5,254,254 | 10/1993 | Shin et al. | 210/616 |
| 5,320,963 | 6/1994 | Knaack et al. | 435/295.1 |
| 5,445,740 | 8/1995 | Malone | 210/618 |
| 5,458,779 | 10/1995 | Odegaard | 210/616 |
| 5,543,039 | 8/1996 | Odegaard | 210/150 |
| 5,593,890 | 1/1997 | Flores-Cotera et al. | 435/295.1 |

FOREIGN PATENT DOCUMENTS

| | | | |
|---|---|---|---|
| 0745562A2 | 12/1996 | European Pat. Off. | C02F 3/30 |
| 2-138960 | 5/1990 | Japan | C17M 1/02 |
| 7-68290 | 3/1995 | Japan | C02F 3/30 |
| 7-68291 | 3/1995 | Japan | C02F 3/30 |
| 7-68292 | 3/1995 | Japan | C02F 3/30 |
| 8-117777 | 5/1996 | Japan | C02F 3/08 |

*Primary Examiner*—David A. Redding
*Attorney, Agent, or Firm*—Burns, Doane, Swecker and Mathis LLP

[57] ABSTRACT

A biochemical reactor utilizing an immobilized carrier which is useful in applications such as denitrification of waste water and includes a circulation conduit within the interior of the biochemical reactor. A feed conduit feeds recirculating fluid through a circulation inlet of the circulation conduit. The feed outlet of the feed conduit is located relative to the circulation inlet opening to direct fluid flowing out of the feed outlet into the circulation conduit to induce a circulation motion of immobilized carriers and fluid into the circulation inlet opening, through the circulation conduit, out of a circulation outlet opening, through the interior of the biochemical reactor, and again into the inlet of the circulation conduit.

29 Claims, 5 Drawing Sheets

BIOCHEMICAL REACTOR

BACKGROUND OF THE INVENTION

1. Field of the Invention

The present invention relates to biochemical reactors and, more particularly, to a biochemical reactor which circulates carriers on which microorganisms are immobilized along with fluid such that biodegradation by the microorganisms may be utilized.

2. Description of the Related Art

Biochemical reactors which circulate fluid are used in a variety of applications, and generally utilize biodegradation performed by microorganisms within the reactor. This biodegradation may be used to produce desired products, to remove specific elements or compounds from ground water and waste water, or to perform conversion of such water. For example, biochemical reactors are commonly used for both nitrification (ammonia removal) and denitrification (nitrate removal).

Traditionally, biological treatment systems have used suspended-growth, continuously stirred biochemical tank reactors, or attached growth systems which use solid media to support the bacteria by which biodegradation is achieved. Such biochemical reactor designs are typified by activated sludge systems that use large water tanks and problematically yield effluents containing large amounts of sludge, which must be removed by yet another treatment process. Other biological reactors include trickling filters or sand filters which are smaller and have lower effluent biological solids content, but are often plagued with media clogging, poor fluid flow characteristics, and loss of active bacteria. In recent years, biochemical reactors have been configured to accommodate immobilized carriers, porous materials that provide a large surface area upon which live microorganisms are immobilized. Due to the microorganisms' affinity to the carrier material, the bacteria may be maintained or confined within the reactor and may be highly concentrated. Biodegradation within a biochemical reactor utilizing such immobilized carriers generally proceeds as raw fluid or influent is fed to the reactor and stirred or agitated so that the liquid comes into contact with the immobilized carriers. Such biochemical reactors which utilize immobilized carriers to obtain biodegradation are typically referred to as "bioreactors."

Bioreactors are capable of performing highly specific reactions by utilizing the biodegradation by the microorganisms. Examples of bioreactor applications include the production of alcohol and antibiotics, and the removal of trace petroleum hydrocarbons and nitrogen from ground water and waste water. A common application of bioreactors is to remove nitrates from ground water, waste water, or salt water. For example, bioreactors are particularly useful in denitrification systems which treat aquatic salt water from commercial aquariums or ground water contaminated with chemical fertilizers.

Problems associated with conventional bioreactors stem from difficulties in efficiently utilizing the immobilized carriers. For instance, immobilized carriers become very buoyant due to gases which are produced during many biodegradation processes. Because of the high buoyancy of the immobilized carriers, it is difficult to continuously stir or circulate the immobilized carriers within the raw fluid, a necessary process to ensure efficient biodegradation. Immobilized carriers in biochemical reactors used in denitrification systems generate nitrogen gas during the biodegradation process and tend to float to the top of the reactor such that they are difficult to stir or circulate within the reactor. When such bioreactors are under high nitrite loading conditions, the carriers actually behave similar to ping-pong balls within stirring water, such that it is difficult to uniformly distribute the immobilized carriers in the reactor to achieve efficient biodegradation. In an attempt to address this problem, conventional bioreactors have incorporated a variety of apparatus and techniques to circulate or stir the immobilized carriers within the fluid inside the bioreactor.

For example, one conventional bioreactor includes an impeller within the bioreactor to stir and disperse the immobilized carriers within the fluid in the reactor. However, immobilized carriers are particularly fragile, and such impellers impart shear stress on the immobilized carriers to such an extent that they can become damaged.

Figure 5:
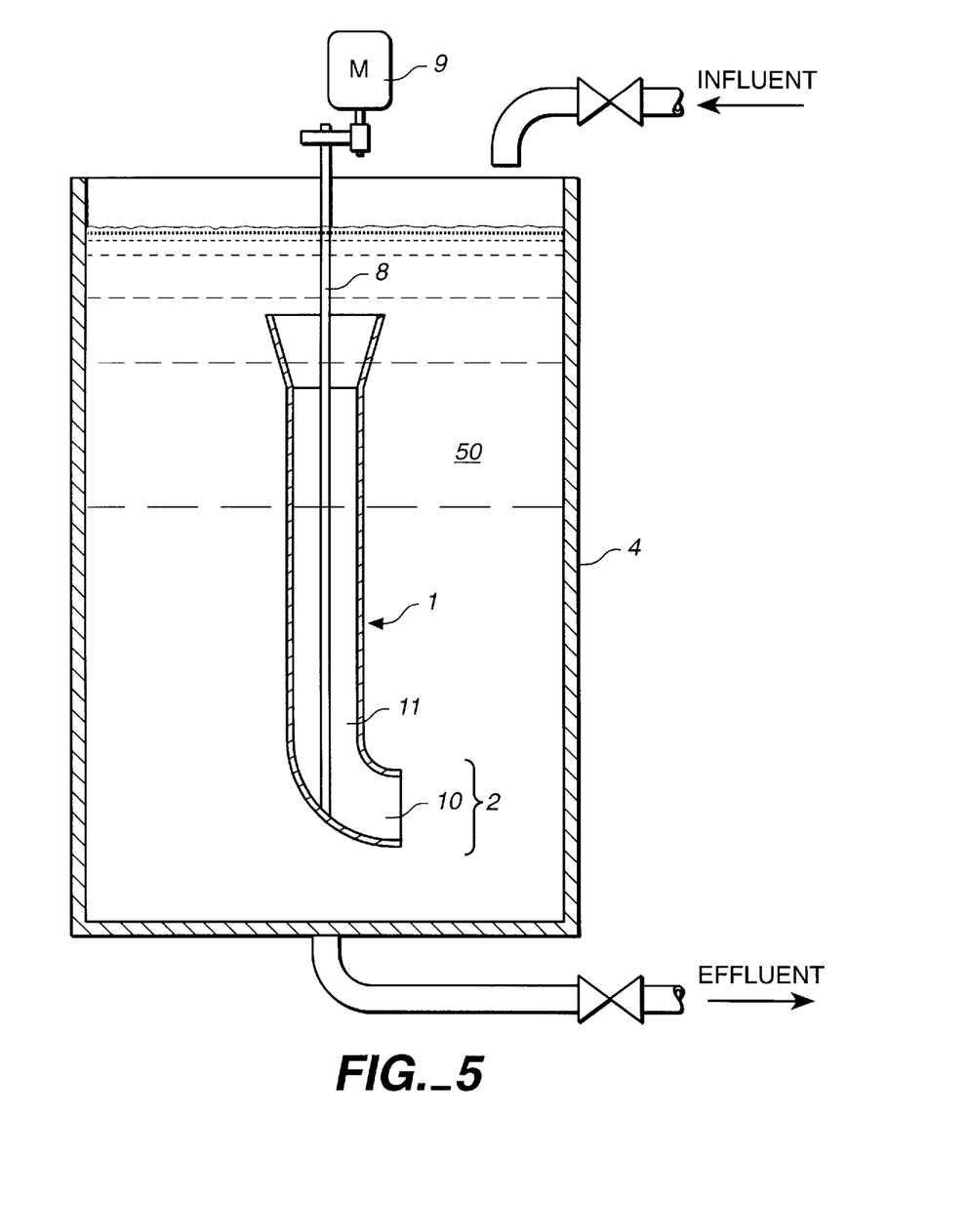
FIG. 5 is a cross-sectional view of a known bioreactor.

Other conventional bioreactors include a centrifugal tube, such as that illustrated in FIG. 5. The conventional bioreactor 50 illustrated in FIG. 5 includes a centrifugal tube 1 having a curved end 2 at which the outlet 10 of the tube is located. The centrifugal tube 1 is mounted on a rotary shaft 8 within the interior of the bioreactor tank 4, and is rotated such that a centrifugal force is generated. This centrifugal force draws the immobilized carriers into the top inlet of the centrifugal tube 1, through the interior length 11 of the tube and out the outlet 10 located near the bottom of the reactor. To create this centrifugal action, the shaft 8 and the centrifugal tube 1 attached thereto must be continuously rotated by a motor 9.

This bioreactor 50 is problematic, especially when adapted for use in large denitrification systems. For example, because the bioreactor 50 includes many rotating parts within the interior of the bioreactor, it is particularly difficult to construct. Furthermore, when using the bioreactor with large denitrification systems, such as that used with commercial aquariums, the centrifugal tube 1 must be extremely large to accommodate the flow rates and denitrification requirements. Because the centrifugal tube 1 must be large in such applications, it has an increased mass and length, and is particularly difficult to rotate and balance. Thus, the moving parts of the bioreactor 50 are made from materials which can accommodate the large forces generated when rotating a large centrifugal tube 1. Such materials are expensive, particularly when they must also be corrosion resistant in salt water. Moreover, when the bioreactor 50 must remove high amounts of nitrates, the centrifugal tube 1 must be rotated faster, which tends to create a vortex within the bioreactor, drawing oxygen into the fluid within the reactor. During the denitrification process, the presence of oxygen within the water seriously undermines the capabilities of the immobilized carriers to remove nitrates from the water. In general, the bioreactor 50 is also difficult to operate and maintain for the reasons described above, and further because it includes a large number of moving parts.

Figure 6:
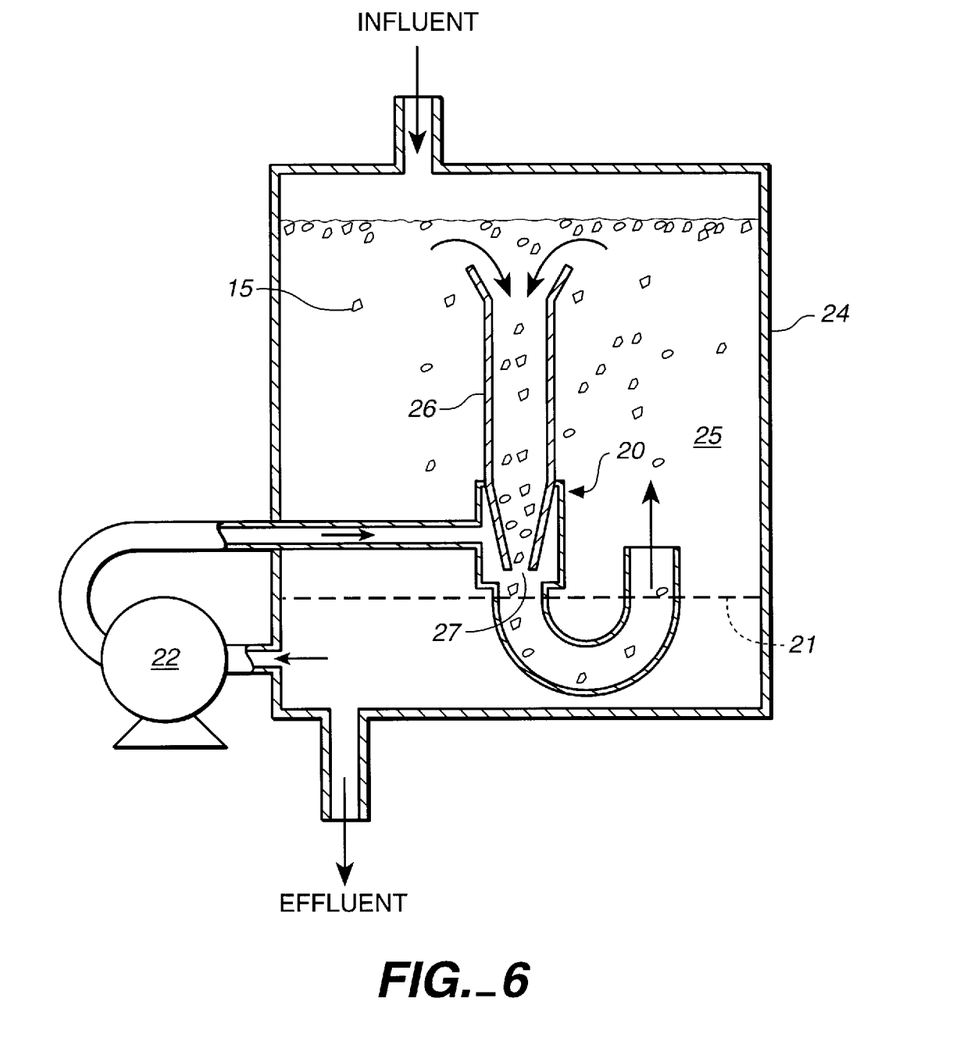
FIG. 6 is a cross-sectional view of another known bioreactor.

Another conventional bioreactor 25 is illustrated in FIG. 6 which includes a liquid current jet mechanism 20 powered by an external pump 22. The bioreactor 25 generally includes a filter 21 which separates the immobilized carriers 15 from the fluid such that the fluid may be drawn from the bioreactor and delivered to the pump 22. The pump 22 located external of the bioreactor vessel 24 thereafter pumps the fluid at a high velocity around a bottom opening 27 of a tube 26 such that immobilized carriers and fluid within the tube 26 are drawn through the bottom opening 27 of the tube by the high velocity fluid.

The liquid current jet mechanism 20 creates flow within the tube 26 and within the interior of the bioreactor vessel 24. However, such liquid current jet mechanism 20 has problems. For instance, the bottom opening 27 of the tube 26 around which the high velocity raw liquid is directed is typically tapered inward to further enhance the suction of immobilized carrier 15 and fluid through the tube 26. This design causes the immobilized carrier 15 to pack-up and choke the bottom opening 27, especially when the bioreactor 25 is used to remove high amounts of nitrates such that the reactor is under a high load. Once the jet mechanism 20 is clogged or packed, the bioreactor must be shut down, drained, and disassembled to unpack the immobilized carriers 15 from the bottom opening 27. In general, any restrictions within the tube 26 are problematic when the bioreactor 25 is under high loads.

In addition, the external pump 22 must generate high flows rates for the jet mechanism 20 to generate the amount of suction necessary to properly and uniformly distribute the immobilized carriers 15 within the bioreactor vessel 24, dictating the use of a large pump for high loads and further decreasing the efficiency of the bioreactor 20.

Furthermore, because the design of the liquid current jet mechanism 20 requires that the jet mechanism be located at the bottom opening 27 of the tube 26, it is particularly difficult to draw buoyant immobilized carriers 15 into the inlet of the tube 26, upstream of the liquid current jet mechanism 20. Thus, the immobilized carriers 15 tend to float and accumulate on the surface of the fluid within the bioreactor vessel 24 before they are drawn into the inlet of the tube 26. This delayed effect results in a non-uniform dispersion of the immobilized carrier within the bioreactor and reduces the efficiency of, for example, denitrification within the bioreactor 25.

Still another problem associated with conventional bioreactors occurs when starting-up the bioreactors. When the start-up process of conventional bioreactors is initiated, the immobilized carriers are generally all located at the bottom of the reactor tank. During the start-up period of conventional bioreactors, it can be difficult to remove or dislodge the immobilized carriers form the bottom of the tank such that they are circulated throughout the bioreactor tank. In fact, the immobilized carriers may behave differently, depending upon the amount o biodegradation required of the carriers and the application. Conventional bioreactors have trouble distributing immobilized carriers which exhibit different characteristics. That is, the bioreactors are not easily adaptable to changing conditions.

Thus, it is apparent that conventional bioreactors are generally inefficient, especially when under high denitrification loads. Furthermore, many conventional bioreactors include complex moving parts which create further constructional and operational problems. The above-described constraints and problems associated with conventional bioreactors has created a need for a solution.

SUMMARY OF THE INVENTION

Generally speaking, the present invention provides a biochemical reactor which uniformly circulates and distributes immobilized carriers and fluid within the bioreactor without incorporating moving parts within the interior of the reactor but which induces circular and helical circulation flow within the interior of the biochemical reactor. The present invention provides a bioreactor that permits realization of the foregoing objects. The bioreactor includes a tank having an interior for holding immobilized carriers and fluid. A circulation conduit is at least partially located within the interior of the tank. The circulation conduit has a circulation inlet opening, and a circulation outlet opening. A feed conduit includes a feed outlet located in a first or second position. The feed outlet is located external of the circulation conduit in the first position. The feed outlet is located within the feed conduit and the feed conduit is located partially through the circulation inlet opening in the second position. The feed outlet is located relative to the circulation inlet opening in the first and second positions to direct fluid flowing out of the feed outlet into the circulation conduit to induce a circulation motion of immobilized carriers and fluid into the circulation inlet opening, through the circulation conduit, out of the circulation outlet opening, through the interior of the tank, and again into the inlet of the circulation conduit. The biochemical reactor also includes a tank inlet for feeding fluid to the tank, and a tank outlet for drawing fluid from the tank.

According to another aspect of the present invention, a biochemical reactor includes a tank having an interior for holding immobilized carriers and fluid. A circulation conduit is at least partially located within the interior of the tank, and the circulation conduit has a circulation inlet opening and a circulation outlet opening. A feed conduit has a feed outlet. At least one of the feed outlet and the circulation inlet opening is movable with respect to the other in at least two different positions. The different positions locating the feed outlet relative to the circulation inlet opening to direct fluid flowing out of the feed outlet into the circulation conduit to induce a circulation motion of immobilized carriers and fluid into the circulation inlet opening, through the circulation conduit, out of the circulation outlet opening, through the interior of the tank, and again into the inlet of the circulation conduit. The biochemical reactor also includes a tank inlet for feeding fluid to the tank, and a tank outlet for drawing fluid from the tank.

In accordance with another aspect of the present invention, a biochemical reactor includes a tank having an interior for holding immobilized carriers and fluid. A circulation conduit is at least partially located within the interior of the tank. The circulation conduit has a circulation inlet opening, and a circulation outlet opening. A feed conduit has a feed outlet located relative to the circulation inlet opening to direct fluid flowing out of the feed outlet into the circulation conduit to induce a circulation motion of immobilized carriers and fluid into the circulation inlet opening, through the circulation conduit, out of the circulation outlet opening, through the interior of the tank, and again into the inlet of the circulation conduit. At least one vane is located adjacent to the circulation outlet to induce immobilized carriers and fluid to helically move about the circulation conduit. The biochemical reactor also includes a tank inlet for feeding fluid to the tank, and a tank outlet for drawing fluid from the tank.

Another aspect of the present invention involves a method of recirculating fluid and immobilized carrier within an interior of a biochemical reactor. The method includes the step of inducing a circulation motion of immobilized carriers and fluid into a circulation inlet opening of a circulation conduit, through the circulation conduit, out of a circulation outlet opening of the circulation conduit, through the interior of the tank, and again into the inlet of the circulation conduit by directing fluid from a feed outlet of a feed conduit into the circulation inlet. The feed outlet is located in one of two positions. The feed outlet is located external of the circulation conduit in a first of the two positions, and the feed conduit is located through the circulation inlet opening in a second of the two positions.

Other objects, advantages and features associated with the present invention will become readily apparent to those skilled in the art from the following detailed description. As will be realized, the invention is capable of other and different embodiments, and its several details are capable of modification in various obvious aspects, all without departing from the invention. Accordingly, the drawings and the description are to be regarded as illustrative in nature, and not limitative.

DETAILED DESCRIPTION OF THE PREFERRED EMBODIMENTS

FIGS. 1–4 shows a biochemical reactor 100 which contains immobilized carriers 201 and a fluid such that biodegradation by microorganisms immobilized on the carriers may be utilized. As described below, the biochemical reactor 100 includes a feed conduit 142 and a circulation conduit 110. A feed outlet 144 of the feed conduit 142 is located relative to a circulation inlet opening 140 of the circulation conduit 110 and directs fluid flow into the circulation conduit to induce a circulation motion of the immobilized carriers 201 and the fluid within the reactor tank 102. The induced circulation motion efficiently and uniformly distributes the immobilized carriers 201 throughout the tank 102. In a preferred embodiment of the present invention, the biochemical reactor 100 is particularly configured for denitrification, the removal of nitrates from ground water, waste water, salt water, or aquarium water.

The biochemical reactor of the present invention may also be used for nitrification or methane fermentation, for example, if the immobilized carrier supports methane generating bacteria. It may also be used for reducing the level of ammonium nitrogen if the immobilized carrier 201 supports nitrifying bacteria. In general, the biochemical reactor 100 is most suitable for applications where an immobilized carrier 201 is circulated within a fluid in the biochemical reactor. However, the biochemical reactor 100 is also suitable for other applications which utilize biodegradation by microorganisms. As such, the biochemical reactor 100 may be used in chemical treatment facilities, filter tanks, and other water purification facilities. Immobilized carriers such as "Fabios" and "Biofiner" that may be used in the biochemical reactor 100 are well known in the art and are available from known establishments such as Yunichika Co., Ltd. and Chiyoda Corp.

Figure 1:
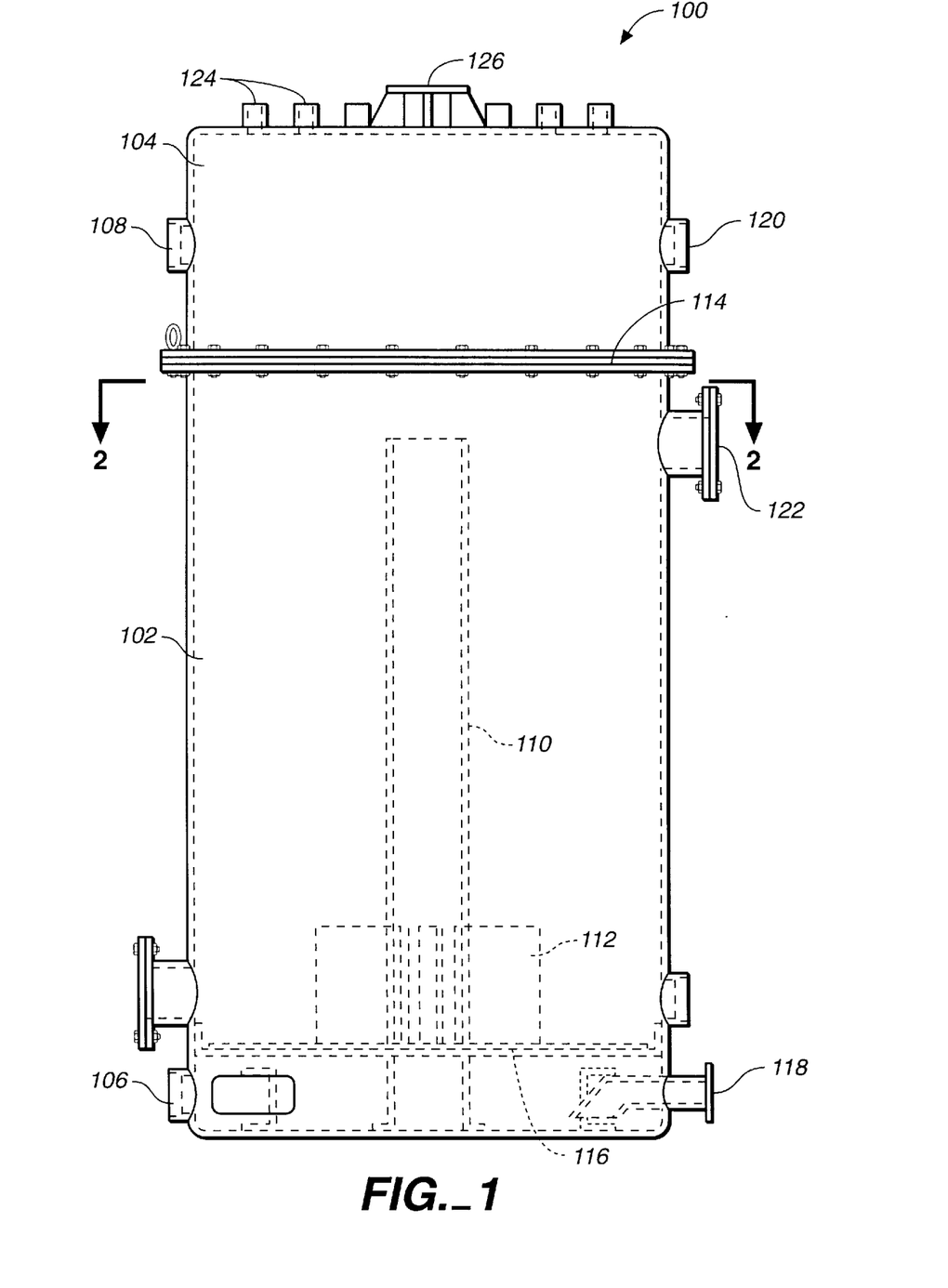
FIG. 1 is a side view of a biochemical reactor according to one embodiment of the present invention.
Figure 3:
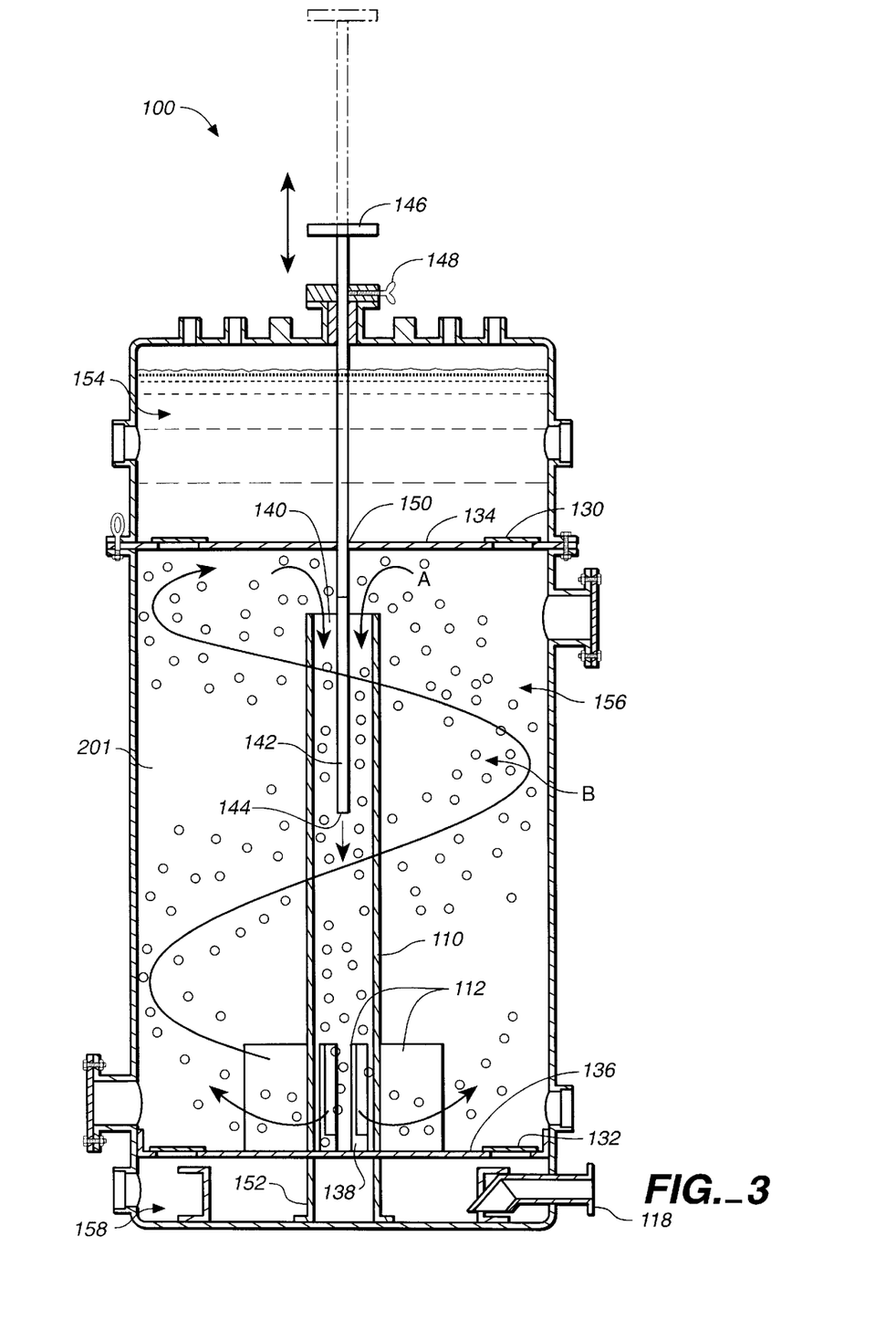
FIG. 3 is a side and sectional operational view of a biochemical reactor according to the present invention.

The biochemical reactor 100 illustrated in FIG. 1 includes a tank 102 having a generally cylindrical shape, although other shapes and configurations may work equally well. The tank 102 is adapted to hold a fluid such as water and the immobilized carriers 201 as illustrated in FIG. 3. The tank 102 includes a tank inlet 106 located near the bottom of the tank, and a tank outlet 108 located near the top of the tank. However, the tank inlet 106 and the tank outlet 108 may be located elsewhere. For example, their respective locations may be switched. The tank inlet 106 and tank outlet 108 are circular holes or ports located within the wall of the tank 102. The tank inlet 106 and outlet 108 may be other configurations well known in the art, such as overflow walls, internal conduits, or hoses.

In operation of the reactor 100, influent, which can be in the form of raw, untreated, contaminated, partially treated, or other fluid, enters the interior of the tank 102 through the tank inlet 106, and treated fluid or effluent exits the interior of the tank through the tank outlet 108. In a preferred embodiment of the bioreactor 100 adapted for denitrification, the size of the tank 102 is proportional to the desired volumetric flow rate of fluid into the inlet 106. For example, if one gallon per minute (gpm) of influent enters the tank inlet 106, and it is desired that the influent have at least a 30 minute retention time within the interior of the tank 102, the tank should have a volumetric capacity of at least 30 gallons, preferably 40–60 gallons, depending upon the capacity of the pumps used with the tank 102.

As shown in FIG. 1, the tank 102 includes a cover 104 in which the tank outlet 108 is located. Although the tank 102 is formed from two pieces, it is contemplated that the tank 102 may be fabricated in one integral piece or from a plurality of pieces so long as the tank holds fluid. However, as shown in FIG. 1, the cover 104 of the tank 102 preferably attaches to a top dividing member 114 near the top of the tank, but below the tank outlet 108.

The top divider 114, as shown in FIG. 3, includes a top disk 134 which spans the width of the cylindrical tank 102 such that it intersects the periphery of the tank. The top divider 114 is substantially similar to a bottom divider 116 illustrated in FIG. 2.

The bottom divider 116 is located towards the bottom of the tank 102 but is located above the tank inlet 106. The bottom divider 116 spans the width of the tank 102 like the top divider 114, but is mounted to the interior surface of the tank 102 and is substantially perpendicular therewith. Although the dividers 114, 116 are each perpendicular with the wall of the tank 102, they need not be so positioned. The dividers 114, 116 may be at an angle or at angles with the wall of the tank 102. Likewise, the dividers 114, 116 need not be flat.

Figure 2:
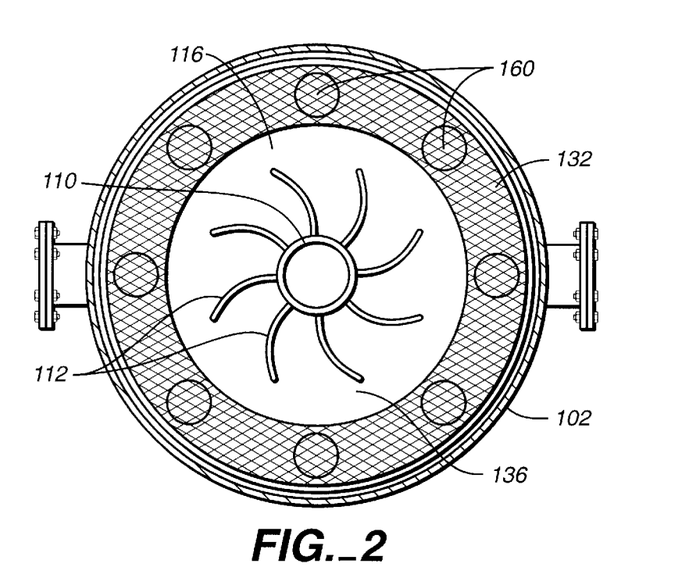
FIG. 2 is a sectional view of the biochemical reactor taken along the line 2—2 of FIG. 1.

FIG. 2 illustrates a top view of the bottom divider 116. As shown in FIG. 2, the bottom divider 116, like the top divider 114, includes a bottom disk 136 and a perforated member 132. The top and bottom disks 134, 136 are generally circular and are defined by flat sheets of fiber reinforced plastic or similar material having a plurality of holes 160 equidistantly or substantially equidistantly spaced near the periphery of the disks. That is, the plurality of holes 160 are located radially outwardly from the center of the disks 134, 136.

The dividers 114, 116 each include the perforated members 130, 132, which according to one embodiment of the present invention are thin and porous screen-like sheets. The perforated members 130, 132 define a perforated area of each of the dividers 114, 116, and are shaped like an annulus, ring, or the region bounded by two concentric circles. The perforated members 130, 132 are sized to cover all of the holes 160 in the top and bottom disks 134, 136, but do not cover the center area of the disks 134, 136.

According to one embodiment of the present invention, the perforated members 130, 132 may be formed from ⅛ inch thick polyvinylchloride (PVC) having ⅛ inch diameter holes. Configured as such, the perforated members 130, 132 function as a screen, filter, seive, strainer, net, mesh, sponge, or other device by which immobilized carriers 201, each having a diameter of approximately ¼ inch, are prevented from passing therethrough. Differently sized and configured perforated members 130, 132 may be used depending upon the size of the immobilized carrier 201. Likewise, the disks 134, 136 may be formed with a series of holes or perforations such that the perforated areas are part of the disks 134, 136. That is, the dividers 114, 116 may be formed from one item which has perforations therein, or may be formed from multiple items such as the disks 134, 136 and the perforated members 130, 132. Furthermore, the perforated area of the dividers 114, 116 need not be located near the periphery of the dividing members, and need not be annularly-shaped.

As illustrated in FIG. 3, the bottom divider 116, by virtue of the perforated member 132 and the holes 160 in the disk 136, allows fluid which is being treated within the biochemical reactor to pass to the second carrier-free zone 158, but prevents the passage of the immobilized carriers 201. The bottom divider 116 also permits influent to pass through the perforated area of the bottom divider 116 into the interior of the tank 102.

As mentioned above, the top divider 114 also includes the disk 134 and the perforated member 130. As such, the top divider 114 prevents the passage of immobilized carriers 201, but allows the fluid being treated to pass through the perforated area such that effluent may be drawn from the tank outlet 108. Although the top divider 134 is formed from two separate items, specifically the disk 136 and the perforated member 132, it is also contemplated that the divider 114, like the divider 116, may be formed from one integral member having perforations therein.

As shown with reference to FIG. 3, the top divider 114 and the bottom divider 116 define a first carrier-free zone 154 above the top divider, a second carrier-free zone 158 below the bottom divider, and a carrier zone 156 in the area located between the two dividers 114, 116 within the tank 102. The carrier zone 156 is the area in which both the immobilized carriers 201 and the fluid being treated by the immobilized carriers are located. As is apparent from FIG. 3, the carrier zone 156 is the area within the biochemical reactor 100 where the immobilized carriers 201 are uniformly or generally uniformly circulated such that biodegradation by the immobilized carriers is utilized.

As illustrated in FIGS. 1, 2, and 3, located within the carrier zone 156 of the biochemical reactor 100 is a circulation conduit 110. However, the circulation conduit may extend outside the carrier zone or even outside the tank 102 and still be within the confines of the present invention. Accordingly, the circulation conduit 110 is at least partially located within the interior of the tank 102.

The circulation conduit 110 illustrated in FIGS. 1, 2, and 3 is a cylindrical and tubular member having an upper end and a lower portion located opposite from the upper end. The circulation conduit 110 also has a circulation inlet opening 140 and a circulation outlet opening 138. The circulation inlet opening 140 is circular and defines the upper end of the cylindrical tube. The circulation outlet opening 138 is located opposite from the circulation inlet opening 140, at the lower portion of the cylindrical tube. According to the embodiment of the biochemical reactor illustrated in FIG. 3, the circulation conduit 110 is positioned along the longitudinal axis of the tank 102 and also along the central axis of the tank 102.

The diameter of the circulation conduit 110 may be ⅓ to ¹⁄₁₅ of the diameter of the tank 102, preferably ⅕ to ¹⁄₁₀, depending upon the desired capacity of the bioreactor 100. For example, one exemplary diameter for the tank is approximately 49 inches and one exemplary diameter of the circulation conduit 110 is 8 inches. Although it is preferable that the circulation conduit 110 be cylindrical, the circulation conduit 110 may possess other shapes. For instance, the circulation conduit 110 may be an oval tube, a tube with changing diameters, or a square tube. The cylindrical tube 110, like the majority of the bioreactor 100 may be made from fiber reinforced plastic. Also, the circulation conduit 110 may possess any desired length depending upon the dimensions of other parts of the reactor.

As shown in FIG. 3, the circulation conduit 110 preferably has a length at least greater than half the distance between the top divider 114 and bottom divider 116. The circulation inlet opening 140 of the circulation conduit 110 permits fluid and immobilized carriers 201 to enter into the circulation conduit, whereas the circulation outlet opening 138 permits the immobilized carriers 201 and fluid to exit the circulation conduit. Accordingly, the area of the circulation inlet opening 140 and the circulation outlet opening 138 should each be large enough to permit the immobilized carrier 201 to pass therethrough.

The circulation outlet opening 138 shown in FIG. 3 is located in the exterior surface of the circulation conduit 110. The bottom end of the circulation conduit 110 is closed off and is immediately adjacent to the bottom disk 136 of the bottom divider 116. The fluid traversing through the circulation conduit 110 is not permitted to immediately enter the second carrier-free area 158 because the disk 136 blocks the passage of the fluid in the area immediately surrounding the periphery of the circulation conduit 110 near the bottom of the tank, except for the holes 160 formed in the disk 136 and covered by the perforated member 132.

As shown in FIG. 3, the circulation outlet opening 138 of the circulation conduit 110 includes a plurality of slit-shaped openings or slots that extend through the wall of the circulation conduit 110 in the lower portion of the circulation conduit 110. In the embodiment of the present invention illustrated in FIG. 3, there are eight slit-shaped openings defining the circulation outlet opening 138. The eight slit-shaped openings can be equidistantly spaced about the periphery of the circulation conduit 110 and together have a rectangular net cross-sectional area at least equal to the circular cross-sectional area of the circulation conduit 110. In a preferred embodiment of the present invention, the net cross-sectional area of the circulation outlet opening 138 is approximately 75 square inches, and the cross-sectional area of the circulation conduit 110 is approximately 50 square inches.

Although the circulation outlet opening 138 illustrated in FIG. 3 may be a plurality of rectangular or slit-shaped openings, other shaped openings are contemplated, such as ovals, circles, squares, curved slits, perforated patterns, and the like, so long as the opening 138 is sufficiently large to permit the immobilized carriers 201 to pass therethrough. The circulation outlet opening 138 has a sufficient area such that the immobilized carriers 201 traversing through the circulation conduit 110 do not pack, choke, or clog near the bottom of the circulation conduit. It is preferred that the net cross-sectional area of the circulation outlet openings 138 be at least 50% greater than the cross-sectional area of the circulation conduit 110 to prevent choking of the immobilized carriers within the circulation conduit 110 at maximum loading conditions. Furthermore, as shown in FIG. 3, the circulation conduit 110 is free from any restrictions or tapers which might initiate clogging or packing of immobilized carriers within the circulation conduit 110.

The circulation of the immobilized carriers 201 and fluid within the biochemical reactor tank 102 is best described with reference to the operation of the biochemical reactor 100 incorporated in a partial assembly of a denitrification system illustrated in FIG. 4.

Figure 4:
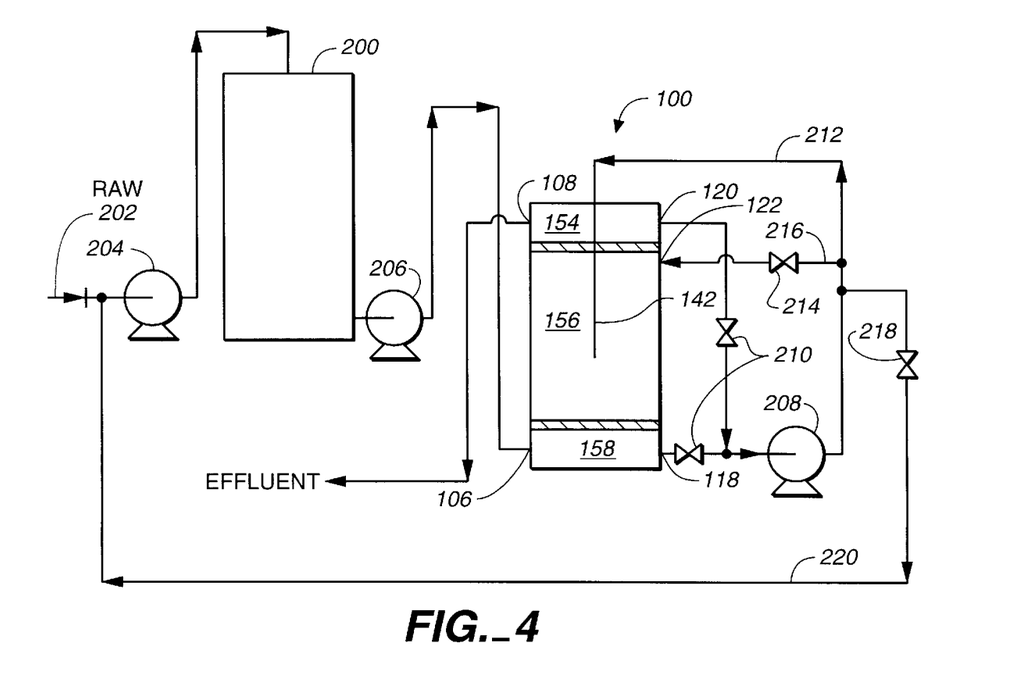
FIG. 4 is a systematic view of a biochemical reactor according to the present invention incorporated into a portion of a denitrification system.

As shown in FIG. 4, the denitrification system includes a deaeration reactor 200 along with the biochemical reactor 100. The deaeration reactor 200 may be an embodiment of the biochemical reactor 100, a series of biochemical reactors 100 or another device for removing oxygen from the raw influent. If the deaeration reactor 200 is a biochemical reactor according to one embodiment of the present invention, it may be used to remove oxygen from the raw influent fed to the system such that nitrates are more efficiently removed by the downstream biochemical reactor 100, as is well known in the art. In general, the denitrification chemistry which occurs during the denitrification process in the biochemical reactor 100 is summarized below.

Denitrification Chemistry (Simplified)

Nitrate Respiration

Hydrolysis Reaction

As shown in FIG. 4, the raw influent is fed to the system at the system inlet 202 where it is pumped into the deaeration reactor 200 by the pump 204 to remove oxygen from the water prior to treatment by the bioreactor 100. In general, the retention time that the raw water should be retained within the deaeration reactor 200 is approximately 20–45 minutes, depending upon the oxygen content of the raw water. However, as indicated by the above denitrification chemistry, the more oxygen removed from the water or the more anoxic the denitrification process, the more efficient the nitrate removal in the subsequent biochemical reactor 100. After sufficient oxygen has been removed from the raw water, the pump 206 pumps the effluent from the deaeration reactor into the inlet 106 of the biochemical reactor 100. As is apparent from the above hydrolysis reaction, methanol must be added to the bioreactor 100 and the deaeration reactor 200, as is well known in the art.

As shown in FIGS. 1, 3, and 4, the inlet 106 is located below the perforated member 132 such that the influent entering the biochemical reactor 100 does not directly feed into the carrier zone 156. The outlet 108 located near the top of the tank 102 is the exit port through which the treated effluent exits the biochemical reactor 100. However, before the effluent may be drawn from the biochemical reactor 100, it is necessary that the influent entering the biochemical reactor 100 be retained and circulated within the reactor such that sufficient nitrates are efficiently removed from the influent fluid. To achieve efficient removal, it is necessary to uniformly circulate the immobilized carriers 201 throughout the carrier zone 156. If the immobilized carriers 201 are stagnant or not circulated within the biochemical reactor 100, the denitrification process can be compromised. To achieve uniform circulation, the present invention incorporates a feed conduit 142, one embodiment of which is illustrated in FIG. 3.

As illustrated in FIG. 3, the feed conduit 142 includes a feed outlet 144. Fluid flow is directed or aimed out of the feed conduit outlet 144 into the circulation conduit 110. The fluid flow emanating from feed outlet 144 is obtained by pumping fluid from either the first recirculation port 120 or the second recirculation port 118. The first recirculation port 120 is located above the first perforated member 130 in the first carrier-free area 154 such that when fluid is drawn from the bioreactor tank 102 by the first recirculation port 120, no immobilized carriers exit the tank. Likewise, the second recirculation outlet 119 is located below the second perforated member 132 in the second carrier-free area 158 such that no immobilized carriers 201 exit the bioreactor tank 102 via the second recirculation outlet 118. As illustrated in FIG. 4, fluid may be drawn from the biochemical reactor tank 102 through the first recirculation port 120, the second recirculation port 118, or both ports. The extent to which fluid is drawn from the first and second recirculation ports 120, 118 may be controlled by adjusting the valves 210 illustrated in FIG. 4.

Once fluid is drawn from the biochemical reactor tank 102 by either the first recirculation port 120 and/or the second recirculation port 118, the pump 208 pumps the fluid along the recirculation line 212 into the feed inlet 146 of the feed conduit 142. Thereafter, the fluid flow is directed out of the feed outlet 144 and into the circulation conduit 110. Thus, a recirculation path of fluid is established through the feed conduit via at least one of the first and second circulation ports 120, 118, the pump 208, and the recirculation line 212.

The extent to which fluid is drawn from the first recirculation port 120 or the second recirculation port 118 generally depends upon the point in time when the denitrification system is operated. Because the immobilized carriers 201 are generally not buoyant at start-up of the biochemical reactor 100, they are generally located at the bottom of the biochemical reactor tank 102, directly above the bottom divider 116. To help initiate the circulation of the immobilized carriers 201 in the carrier zone 156 of the biochemical reactor 100 at start-up, approximately 80% of the recirculation flow is drawn from the first recirculation port 120 and 20% from the second recirculation port 118 such that the immobilized carrier 201 is drawn more toward the first perforated member 130 than the second perforated member 132. After the immobilized carriers 201 have begun to circulate, generate gas, and become more buoyant, the operation of the biochemical reactor 100 reaches "steady state." At steady state, it is preferred that the first recirculation port 120 draw approximately 40% of the recirculation fluid and the second recirculation port 118 draw approximately 60% of the recirculation fluid.

Steady state may be reached when operating the denitrification system in a "batch" mode, or when operating the denitrification system in a continuous flow mode. Because the biochemical reactor 100 is more efficient than past biochemical reactors and is easily controlled, it may advantageously be operated in a continuous flow mode, whereas past biochemical reactors primarily operated only in batch modes.

As illustrated in FIG. 3, the second recirculation port 118 may be formed by a tube whose inlet is located within the second carrier-free zone 158. Also, the end portion of the second recirculation port 118 includes a bend such that the inlet opening to the second recirculation port within the second carrier-free zone 158 is angled downwardly and located adjacent to the bottom of the tank 102, to further prevent the drawing of immobilized carrier towards the bottom perforated member 132.

As illustrated in FIG. 4, the recirculation flow pumped by the pump 208 may also be routed back to the system inlet 202 of the denitrification system by opening the valve 218 connected to the line 220. This routing back to the system inlet 202 is typically employed during start-up.

The feed conduit 142 illustrated in FIG. 3 is movable in a vertical direction along at least a portion of the longitudinal extent of the circulation conduit 110 as that the feed outlet 144 is movable with respect to the circulation inlet opening 140. The feed outlet 144 of the feed conduit may be positioned so that it extends through the circulation inlet opening 140 of the circulation conduit 110, whereby the inlet opening 140 is located at the position illustrated by reference letter B in FIG. 3. In position B, the feed conduit 142 extends directly through the circulation inlet opening 140, preferably directly along the center axis and longitudinal axis of the circulation conduit 110. Thus, the feed conduit 142 is parallel with the circulation conduit 110. The feed conduit 142 is preferably rod-shaped or a cylindrical and hollow tube. Because the feed conduit 142 is movable or adjustable, the feed outlet 144 may be removed from the interior of the circulation conduit 110 such that the feed outlet 144 is located exterior of the circulation conduit 110, and is located at the position illustrated by reference letter A in FIG. 3. Thus, the feed conduit 142 is adjustable and movable such that the feed outlet 144 is movable between positions A and B.

The feed conduit 142 passes through the center opening 126 in the cover 104 of the tank 102. The feed conduit 142 then passes through an aperture 150 located in the top divider 134 such that the feed outlet 144 is positionable directly above or adjacent to the inlet of the circulation conduit 110 at position A. The aperture 150 located within the top divider 134 is for receiving the feed conduit 142. Preferably, the aperture 150 includes a seal (not shown) which prevents immobilized carriers 201 from passing through any space between the top divider 134 and the exterior surface of the feed conduit 142.

The position of the feed conduit 142 may be adjusted or moved by engaging and disengaging a mechanism for moving the feed conduit 142. The mechanism or means for moving the feed conduit 142 illustrated in FIG. 3 is simply a threaded clasp-type member 148 which applies a force against the exterior surface of the feed conduit 142 to hold it in place such that the feed conduit may be movably raised or lowered. In this manner, the feed conduit 142 may be moved vertically up and down within the interior of the circulation conduit 110, exterior of the circulation conduit 110, or in and out of the circulation conduit. Although the illustrated means for moving the feed conduit 142 is the illustrated threaded clasp-type member 148, other means are contemplated such as a motor, a latching type mechanism, a ratcheting mechanism, a pulley, gears, an interference fit, or other similar devices known in the art.

As illustrated in FIG. 3, the feed conduit 142 directs the recirculation fluid out of the feed outlet 144 into the circulation conduit 110. In position B, the feed outlet 144 is located within the circulation conduit 110 and the feed conduit 142 extends partially through the circulation inlet opening 140. In position B, the feed outlet 144 is located relative to the circulation inlet opening 140 to direct fluid flowing out of the feed outlet 144 into the circulation conduit 110 to induce a circulation motion of immobilized carriers 201 and fluid into the circulation inlet opening 140 of the circulation conduit 110, through the circulation conduit 110, out of the circulation outlet opening 138, through the interior of the tank 102, and again into the circulation inlet opening 140 of the circulation conduit 110. This effect is called induced flow. That is, by directing the fluid flow out of the feed outlet 144 and into the circulation conduit 110 through the opening of the circulation conduit, the volumetric flow rate of the immobilized carriers 201 and fluid through the circulation conduit 110 is enhanced.

The feed conduit 142 is preferably located such that the feed outlet 144 is within the interior of the circulation conduit 110 during the above-described start-up period. Thus, during the start-up or beginning operation of the biochemical reactor 100, it is preferable that the feed outlet 144 be positioned towards the bottom of the circulation conduit 110, for example below the position B, such that the feed outlet 144 is closer to the circulation outlet opening 138 than the circulation inlet opening 140. This is preferable because the recirculation fluid exiting the feed outlet 144 will assist in sweeping or carrying the immobilized carriers 201 off the bottom of the bottom divider 116 at start-up.

It is preferable that the feed outlet 144 be located exterior of the circulation conduit during the normal or steady state operation of the biochemical reactor 100. Thus, after the immobilized carriers 201 become buoyant due to the denitrification reactions, the feed conduit 142 is preferably moved vertically upward such that the feed outlet 144 is located external of the circulation conduit 110, for example one to two inches above the circulation inlet opening 140. When the feed outlet 144 is located external of the circulation conduit, the induced flow effect is greater than when the feed outlet 144 is located within the interior of the circulation conduit 110. Thus, in the position A, where the feed outlet 144 is external of the circulation conduit 110, the feed outlet 144 is located relative to the circulation inlet opening 140 to direct fluid flow out of the feed outlet 144 into the circulation conduit 110 to induce a circulation motion of the immobilized carrier 201 and fluid into the circulation inlet opening 140, out of the circulation outlet opening 138, through the interior of the tank 102, and again into the inlet 140 of the circulation conduit 110. This induced flow effect through the circulation conduit 110 causes a circular pattern of flow into and out of the circulation conduit which improves the efficiency of the biochemical reactor 100. The induced flow effect draws the immobilized carriers 201 into the circulation conduit 110 at a greater flow rate than that exiting the feed outlet 144. For example, according to one embodiment of a bioreactor 100 having the dimensions described herein, if the inlet influent volumetric flow rate into the reactor 100 were one gpm, and the recirculation volumetric flow rate exiting the feed outlet 144 were 10 gpm, the induced volumetric flow rate of immobilized carriers 201 and fluid through the circulation conduit 110 would be approximately 40 to 50 gpm due to this induced flow effect. Under similar conditions, the conventional liquid current jet mechanism 20 illustrated in FIG. 6 induces substantially less circulation flow than the bioreactor 100 according to the present invention.

The above-described induced flow effect of the present invention uniformly or generally uniformly disperses the immobilized carrier 201 throughout the carrier zone 156 so that the immobilized carriers 201 are not stagnant within the reactor tank 102. Because the induced flow effect causes the volumetric circulation flow rate of the immobilized carriers 201 and fluid through the circulation conduit 110 to be many times greater than the volumetric fluid flow from the feed outlet 144, the bioreactor 100 requires less power than previous bioreactors. Thus, the biochemical reactor 100 is more efficient than conventional bioreactors, especially at high loads. Hence, the biochemical reactor 100 occupies less space than conventional biochemical reactors while handling equal loading.

In one embodiment of the bioreactor 100, the circulation inlet opening 140 has a circulation inlet cross-sectional area of a predetermined relationship to the feed outlet cross-sectional area such that when fluid flow is directed out of the feed outlet 144 external of the circulation conduit 110, the volumetric circulation flow rate of immobilized carriers and fluid through the circulation conduit is at least three times greater than a volumetric flow rate of fluid flow from the feed outlet, preferably 4 to 10 times greater. According to one embodiment, the circulation conduit inlet cross-sectional area may be at least four times greater than the feed outlet cross-sectional area, preferably 10 times greater. In general, the velocity of the fluid down the circulation conduit 110 must be sufficient to overcome the buoyancy of the immobilized carriers 210.

Because the induced circulation flow through the circulation conduit 110 varies when the location of the feed outlet 144 is varied, the induced circulation flow may be controlled by moving the feed conduit 142. Accordingly, optimal conditions can be chosen for the biological process by simply varying the location of the feed conduit 142 and the amount of flow exiting the feed outlet 144. Alternatively, the circulation inlet opening 140 may be moved relative to the feed outlet 144, or both the feed outlet 144 and the circulation inlet opening 140 may be moved simultaneously or in steps.

The embodiment of the present invention depicted in FIGS. 1–4 also includes the vanes 112 located adjacent the outlet 138 of the circulation conduit 110. The vanes 112 cause the immobilized carrier 201 and fluid exiting the circulation outlet openings 138 to enter into a helical pattern as they recirculate through the carrier zone 156. That is, the vanes 112 direct the immobilized carriers 201 so that they rotate about the longitudinal axis of the circulation conduit 110 while also circulating through the interior of the circulation conduit and the interior of the tank 102. In this manner, the immobilized carriers 201 are even further uniformly distributed throughout the carrier zone in the biochemical reactor 100.

As shown in FIG. 2, there are preferably eight curved vanes 112, each immediately adjacent a respective one of the openings forming the circulation outlet opening 138. The vanes 112 are attached to the exterior surface of the circulation conduit in a manner well known in the art, such as by fiber reinforced plastic. Alternatively, the vanes 112 may be spaced from the circulation opening 138. The vanes 112 are preferably curved to help induce the helical movement of the immobilized carrier and fluid about the circulation conduit. Although the plurality of vanes 112 illustrated in FIGS. 2 and 3 are preferred, other apparatus for helically moving the immobilized carriers 201 in fluid motion about the circulation conduit 110 are contemplated, such as one helically shaped blade at least partially extending around the periphery of the circulation conduit 110. Similarly, a straight, curved, or angled blade, plate, or fin may be used to induce the helical motion of the immobilized carriers 201 and fluid.

Alternatively, or in addition to the vanes 112, a stream of fluid may be directed tangentially into the tank 102, preferably within the carrier zone 156, to cause the immobilized carrier 201 and fluid to helically move about the circulation conduit 110. The circulation outlet openings 138 formed in the circulation conduit 110 may also be a series of tubes or pipes extending from the circulation conduit 110 in an angled manner to induce helical motion to the immobilized carriers 201 and fluid. As also shown in FIGS. 2 and 3, the vanes 112 preferably do not extend into the perforated member 132 such that the immobilized carrier 201 and fluid exiting the circulation outlet openings 138 are not forced to immediately "bounce" or reflect off the sides of the interior surface of the tank 102.

As shown in FIG. 1, the biochemical reactor 100 also includes a jet opening 122 located immediately below the top divider 114 which is advantageous when the biochemical reactor 100 is under high nitrate loading. During high nitrate loading conditions, the immobilized carriers 201 become very buoyant. To ensure that the immobilized carriers 201 are drawn into the circulation conduit 110 during high nitrate loading conditions, a jet valve 214 depicted in FIG. 4 may be opened or programmed to open during such conditions such that a jet of recirculation fluid is aimed directly underneath the top divider 116 to further agitate the immobilized carrier 201 and improve the efficiency of operation of the biochemical reactor 100.

It may now be appreciated that the present invention provides a biochemical reactor which is more efficient than conventional biochemical reactors.

Further the present invention provides a biochemical reactor in which immobilized carriers within the reactor do not become choked or clogged within the reactor.

Still further, the present invention provides a biochemical reactor which does not require high pumping rates, as compared to conventional biochemical reactors, to uniformly distribute immobilized carriers within the reactor.

In the biochemical reactor the circulation flow of immobilized carriers and raw fluid may be easily controlled to, thereby, provide a biochemical reactor which may adapt to different operational conditions.

As is apparent from the foregoing, the biochemical reactor 100 is of a much simpler design than conventional biochemical reactors, particularly since it does not include the same type of moving or rotating parts within the reactor tank 102 as in other known devices. Because the circulation tube 110 is free from restrictions and because the fluid flow out of the feed conduit 142 continuously agitates the immobilized carriers 201 within the circulation conduit, the chances of packing or clogging of carriers within the circulation conduit is substantially reduced, particularly at high loads. In addition, because the reactor is designed to effect relative movement between the feed conduit 142 and the circulation inlet opening 140, the amount and pattern of induced circulation flow may be controlled by simply changing the location of the feed outlet 144 relative to the circulation inlet opening 140. Thus, the biochemical reactor is adaptable to changing operational parameters, such as changes in the buoyancy of the immobilized carriers 201. Accordingly, it is apparent that the biochemical reactor 100 offers many advantages over conventional biochemical reactors. As will be appreciated by those in the art, the biochemical reactor 100 is amenable to many different applications in which conventional biochemical reactors are used.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A biochemical reactor comprising:

a tank having an interior for holding immobilized carriers and fluid;

a circulation conduit at least partially located within said interior of said tank, said circulation conduit having a circulation inlet opening, and a circulation outlet opening;

a feed conduit having a feed outlet, said feed outlet being located in one of a first position and a second position relative to the circulation conduit, said feed outlet being located external of said circulation conduit and positioned to direct fluid flowing out of said feed outlet through the circulation inlet opening in said first position, said feed outlet being located within said circulation conduit with said feed conduit extending through said circulation inlet opening in said second position, said feed outlet being located relative to said circulation inlet opening in said first and second positions to direct fluid flowing out of said feed outlet into said circulation conduit to induce a circulation motion of immobilized carriers and fluid into said circulation inlet opening, through said circulation conduit, out of said circulation outlet opening, through said interior of said tank, and again into said circulation inlet opening;

a tank inlet for feeding fluid to the tank; and a tank outlet for drawing fluid from the tank.

2. The biochemical reactor according to claim 1, further comprising means for helically moving immobilized carriers and fluid about said circulation conduit.

3. The biochemical reactor according to claim 2, wherein said means for helically moving is at least one vane located adjacent to said circulation outlet opening.

4. The biochemical reactor according to claim 1, wherein said feed outlet is movable with respect to said circulation inlet opening.

5. The biochemical reactor according to claim 1, wherein said circulation conduit has a circulation conduit cross-sectional area, and said circulation outlet opening has a net cross-sectional area greater than said circulation conduit cross-sectional area.

6. The biochemical reactor according to claim 1, wherein said feed outlet has a feed outlet cross-sectional area, and said circulation inlet opening has a circulation inlet cross-sectional area at least 4 times greater than said feed outlet cross-sectional area.

7. The biochemical reactor according to claim 1, wherein said feed outlet extends along a central axis of said circulation conduit.

8. The biochemical reactor according to claim 1, wherein said feed outlet has a feed outlet cross-sectional area, and said circulation inlet opening has a circulation inlet cross-sectional area of a predetermined relationship to said feed outlet cross-sectional area, wherein when fluid flow is directed out of said feed outlet in said first position a volumetric circulation flow rate of immobilized carriers and fluid through said circulation conduit is at least three time greater than a volumetric flow rate of fluid flow from said feed outlet.

9. The biochemical reactor according to claim 1, further comprising a first divider having a perforated area, said first divider being located between said circulation inlet opening and said tank inlet for separating fluid from the immobilized carriers, and a second divider having a perforated area, said second divider being located between said circulation outlet opening and said tank outlet for separating fluid from the immobilized carriers.

10. The biochemical reactor according to claim 9, wherein said first and second dividers define an immobilized carrier zone within said interior of said tank for confining said immobilized carriers.

11. The biochemical reactor according to claim 9, wherein said perforated areas are annulus-shaped.

12. The biochemical reactor according to claim 9, wherein said first divider includes an aperture that receives said feed conduit.

13. The biochemical reactor according to claim 9, further comprising a first recirculation port located above said first divider and outside of said carrier zone for removing fluid from said tank for eventual recirculation back to said tank through said feed conduit, and a second recirculation port located below said second divider and outside said carrier zone for removing fluid from said tank for eventual recirculation back to said tank through said feed conduit.

14. The biochemical reactor according to claim 1, wherein the circulation conduit is a cylindrical tube having an upper end and a lower portion located opposite from said upper end, said circulation inlet opening being a circular opening defining said upper end of said cylindrical tube, and said circulation outlet opening being defined by at least one radial opening in said cylindrical tube located at said lower portion.

15. The biochemical reactor according to claim 1, wherein said circulation conduit includes an interior and said circulation outlet opening is defined by a plurality of slits communicating the interior of said circulation conduit with said interior of said tank, said slits being substantially equally spaced about a periphery of said circulation conduit.

16. The biochemical reactor according to claim 1, wherein said circulation outlet opening has a net cross-sectional area greater than the cross-sectional area of the circulation conduit.

17. The biochemical reactor according to claim 16, wherein said circulation outlet opening has a net cross-sectional area and said circulation conduit has a circulation conduit cross-sectional area, said net cross-sectional area being at least 50% greater than said circulation conduit cross-sectional area.

18. The biochemical reactor according to claim 1, further comprising means for moving said feed conduit.

19. The circulation conduit according to claim 1, wherein said circulation conduit is located completely within said tank.

20. A biochemical reactor comprising:

a tank having an interior for holding immobilized carriers and fluid;

a circulation conduit at least partially located within said interior of said tank, said circulation conduit having a circulation inlet opening and a circulation outlet opening;

a feed conduit having a feed outlet, at least one of said feed outlet and said circulation inlet opening being movable with respect to the other so that the feed outlet and the circulation inlet opening are positionable in two different relative positions with respect to one another, said two different positions locating said feed outlet relative to said circulation inlet opening to direct fluid flowing out of said feed outlet into said circulation conduit to induce a circulation motion of immobilized carriers and fluid into said circulation inlet opening, through said circulation conduit, out of said circulation outlet opening, through said interior of said tank, and again into said circulation inlet opening;

a tank inlet for feeding fluid to the tank; and a tank outlet for drawing fluid from the tank.

21. The biochemical reactor according to claim 20, further comprising means for helically moving immobilized carriers and fluid about said circulation conduit.

22. The biochemical reactor according to claim 20, wherein in a first of said two different positions said feed outlet is located external of said circulation conduit.

23. The biochemical reactor according to claim 20, wherein in a second of said two different positions said feed outlet is located within the interior of the circulation conduit.

24. The biochemical reactor according to claim 20, wherein said circulation inlet opening is stationary and said feed outlet is movable with respect to said circulation inlet opening.

25. A biochemical reactor comprising:

a tank having an interior for holding immobilized carriers and fluid;

a circulation conduit at least partially located within said interior of said tank, said circulation conduit having a circulation inlet opening, and a circulation outlet opening;

a feed conduit having a feed outlet, said feed outlet being located relative to said circulation inlet opening to direct fluid flowing out of said feed outlet into the circulation conduit to induce a circulation motion of immobilized carriers and fluid into said circulation inlet opening, through said circulation conduit, out of said circulation outlet opening, through said interior of said tank, and again into said circulation inlet opening;

at least one vane located adjacent to said circulation outlet to induce immobilized carriers and fluid to helically move about said circulation conduit;

a tank inlet for feeding fluid to the tank; and a tank outlet for drawing fluid from the tank, wherein said feed outlet is movable with respect to said circulation inlet opening so that the feed outlet is positionable in two different positions with respect to the circulation inlet opening, a first position of said two positions locating said feed outlet external of said circulation outlet and a second position of said two positions locating said feed outlet within said interior of said circulation conduit.

26. The biochemical reactor according to claim 25, wherein said vane is curved.

27. A method of recirculating fluid and immobilized carrier within an interior of a biochemical reactor, the method comprising inducing a circulation motion of immobilized carriers and fluid into a circulation inlet opening of the circulation conduit, through said circulation conduit, out of a circulation outlet opening of said circulation conduit, through said interior of said tank, and again into said circulation inlet opening by directing fluid from a feed outlet of a feed conduit into the circulation conduit, said feed outlet being located in one of a first position and a second position with respect to said circulation conduit, said feed outlet being located external of said circulation conduit and in a position to direct fluid flowing out of said feed outlet through the circulation inlet opening in said first position, said feed outlet being located within said circulation conduit with said feed conduit extending through the circulation inlet opening in said second position.

28. The method according to claim 27, further comprising the step of directing the immobilized carriers and fluid in a helical path about said circulation conduit.

29. The method according to claim 27, further comprising the step of moving the feed conduit to vary an amount of induced circulation.

* * * * *